United States Patent [19]

Mueller et al.

[11] Patent Number: 5,298,514
[45] Date of Patent: Mar. 29, 1994

[54] PHENOLIC THIOETHERAMIDES

[75] Inventors: Richard A. Mueller, Glencoe; Richard A. Partis, Evanston, both of Ill.

[73] Assignee: G. D. Searle & Co., Chicago, Ill.

[21] Appl. No.: 943,166

[22] Filed: Sep. 10, 1992

Related U.S. Application Data

[63] Continuation of Ser. No. 579,124, Sep. 7, 1990, abandoned.

[51] Int. Cl.$^5$ .................... A61K 31/44; C07D 211/72
[52] U.S. Cl. ........................................ 514/357; 546/337
[58] Field of Search ........................ 546/337, 357

[56] References Cited

U.S. PATENT DOCUMENTS

| | | | |
|---|---|---|---|
| 4,029,812 | 6/1977 | Wagner et al. | 424/298 |
| 4,076,841 | 2/1978 | Wagner et al. | 424/324 |
| 4,078,084 | 3/1978 | Wagner et al. | 424/324 |
| 4,153,803 | 5/1979 | Thiele et al. | 560/57 |
| 4,621,098 | 11/1986 | Umminger et al. | 514/562 |
| 4,663,333 | 5/1987 | Mueller et al. | 514/346 |
| 4,711,903 | 12/1987 | Mueller et al. | 514/381 |
| 4,755,524 | 7/1988 | Mueller et al. | 514/381 |
| 4,857,558 | 8/1989 | Mueller | 424/298 |

FOREIGN PATENT DOCUMENTS

| | | | |
|---|---|---|---|
| 0131221 | 1/1985 | European Pat. Off. | C07C 149/00 |
| 0190682 | 1/1986 | European Pat. Off. | C07C 149/36 |
| 0190685 | 1/1986 | European Pat. Off. | C07D 295/18 |
| 0372409 | 12/1989 | European Pat. Off. | A61K 31/44 |
| 0372410 | 12/1989 | European Pat. Off. | A61K 31/495 |
| 1936463 | 2/1971 | Fed. Rep. of Germany. | |
| 1557622 | 12/1979 | United Kingdom | C07D 213/60 |

OTHER PUBLICATIONS

Goodman and Gilman's, The Pharmacological Basis of Therapeutics (7th Edition, 1985), pp. 660–673.
Badwey, J. A., et al., "cis-Polyunsaturated fatty acids induce high levels of superoxide production by human neutrophils," *J. Biol. Chem.*, 256:12640–12643, (1981).
Carroll E. Cross, et al. "Oxygen Radicals and Human Disease," *Annals of Internal Medicine*, vol. 107, No. 4, Oct., 1987, pp. 526–545, U.S.A.
Peter A. Ward, et al. "Oxygen Radicals, Inflammation, and Tissue Injury," *Free Radical Biology and Medicine*, vol. 5, 1988, pp. 403–408, U.S.A.
Virginia L. Shepherd "The Role of the Respiratory Burst of Phagocytes in Host Defense," *Seminars in Respiratory Infections*, vol. 1, No. 2, Jun., 1986, pp. 99–106, U.S.A.

(List continued on next page.)

Primary Examiner—Marianne M. Cintins
Assistant Examiner—Catherine Scalzo
Attorney, Agent, or Firm—Roberta L. Hastreiter; Roger A. Williams

[57] ABSTRACT

The present invention relates to phenolic thioetheramides of the formula

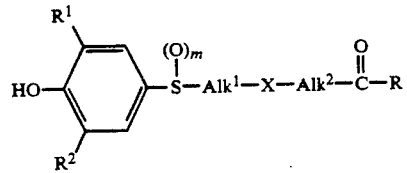

wherein $R^1$ and $R^2$ are tert-alkyl or phenyl, $Alk^1$ and $Alk^2$ are alkylene; X is sulfur or oxygen, m is 0, 1, or 2; and R is

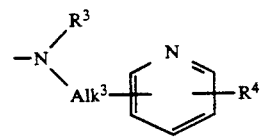

a)

wherein $R^3$ and $R^4$ are hydrogen or alkyl and $Alk^3$ is alkylene.

19 Claims, No Drawings

OTHER PUBLICATIONS

Rakesh C. Kukreja, et al. "PGH Synthase and Lipoxygenase Generate Superoxide in the Presence of NADH or NADPH," *Circulation Research*, vol. 59, No. 6, Dec., 1986, pp. 612–619, U.S.A.

K. Katayana, et al. "In vitro effect of N-methoxy-3-(3,5-diert-butyl-4-hydroxy-benzylidene)-2-pyrrolidone (E-5110), a novel nonsteroidal anti-inflammatory agent, on generation of some inflammatory mediators," *Agents and Actions*, vol. 21, ¾, 1987, pp. 269–271, Switzerland.

P. Biemond, et al. "Diminished Superoxide Production of Synovial Fluid Neutrophils in Patients with Rheumatoid Arthritis Following Piroxicam Treatment," *Scand J. Rheumatology*, 19, 1990, pp. 151–156, Netherlands.

W. Kreutner, et al. "Antiallergy Activity of Sch 37224, a New Inhibitor of Leukotriene Formation," *The Journal of Pharmacology and Experimental Therapeutics*, vol. 247, No. 3, 1988, pp. 997–1003, U.S.A.

A. Cenetti, et al. "Superoxide anion production by circulating polymorphonuclear leucocytes in rheumatoid arthritis," *Clinical rheumatology*, 9, No. 1, 1990, pp. 51–55, Italy.

D. E. Auer, et al. "Superoxide production by stimulated equine polymorphonuclear leukocytes inhibition by anti-inflammatory drugs," *J. vet. Pharmacol. Therap.*, 13, 1990, pp. 59–66, Australia.

Jeffrey R. Kanofsky "Singlet Oxygen Production by Biological Systems," *Chem.-Biol. Interactions*, 70, 1989, pp. 1–28, Ireland.

PHENOLIC THIOETHERAMIDES

This is a continuation of application Ser. No. 07/579,124, filed Sep. 7, 1990 now abandoned.

BACKGROUND OF THE INVENTION

1. Field of the Invention

The present invention relates to phenolic thioetheramides and more particularly relates to the novel compounds of formula I which are specific 5-lipoxygenase inhibitors and are useful, for example, as anti-inflammatory, and anti-allergy agents. Compounds of the present invention may be useful in treating arthritis, asthma, and psoriasis. Compounds of the present invention which stimulate or modulate superoxide generation may be useful as adjunctive therapeutic agents in the treatment of infections. Those compounds which inhibit superoxide generation may be useful in treating conditions in which superoxide radicals are involved.

2. Background Information and Related Art

It is well recognized that arachidonic acid, an essential unsaturated fatty acid, is enzymatically oxygenated to various products, including, prostaglandins, thromboxanes, the 5-, 11-, 12- and 15-hydroxyeicosatetraenoic acids (HETEs, DIHETEs) and hydroperoxyeicosatetraenoic acids (HPETEs) and the leukotrienes, all of which have potent physiological effects. The leukotrienes, which are produced via the 5-lipoxygenase pathway, are the major contributors to the onset of the symptoms of asthma, and mediators for immediate hypersensitivity reactions, inflammation and other allergic responses.

Leukotrienes are found in inflammatory exudates and are involved in the process of cellular invasion during inflammation. The term "leukotrienes" is used as a generic term to describe a class of substances, such as slow-reacting substance (SRS) which is an important mediator in asthma and other hypersensitivity reactions. Immunologically generated SRS is usually referred to as slow-reacting substance of anaphylaxis (SRS-A). SRS-A consists of leukotrienes (LT) known as $A_4$, $B_4$, $C_4$, $D_4$, and $E_4$ $LTC_4$ is at least 100 times more potent than histamine in causing long lasting bronchoconstricting effects. The leukotrienes also increase vascular permeability and cause decreased cardiac output and impaired ventricular contraction. $LTB_4$ may be an important mediator of inflammation in, for example, inflammatory bowel disease.

Chemotaxis is a reaction by which the direction of migration of cells is determined by substances in their environment. It is one of the major processes bringing leukocytes from the blood to an inflammatory site, whether the inflammation is caused by an infectious agent, allergic challenge, or other pro-inflammatory stimuli. $LTB_4$ is not only chemotactic for neutrophils and monocytes, but is also highly active in stimulating eosinophil locomotion. $LTB_4$ also stimulates calcium influx and aggregation of polymorphonuclear leukocytes and $LTB_4$ may, thus, play an important role in mediating both acute and chronic inflammation.

Rheumatoid spondylitis is characterized by an acute neutrophil flareup in the joint which is associated with elevated levels of $LTB_4$. $LTB_4$ is also present in gouty effusions; and exposure to urate crystals is known to stimulate $LTB_4$ production by neutrophils. Accordingly, the 5-lipoxygenase inhibitors of the present invention through inhibition of neutrophil attraction and activation in arthritic joints should reduce the protease and oxidative burden believed responsible for joint destruction in arthritic diseases.

Aspirin and the other non-steroidal anti-inflammatory agents (NSAIDs) such as indomethacin, ibuprofen, fenoprofen, and the like, inhibit the synthesis of prostaglandins via the cyclooxygenase pathway of arachidonic acid metabolism. These prostaglandin synthetase inhibitors generally exhibit anti-inflammatory, antipyretic and analgesic activity, and are widely used in the treatment of arthritis. The non-steroidal anti-inflammatory agents can lead to the formation of additional pro-inflammatory derivatives of arachidonic acid produced through the 5-lipoxygenase pathway which play a role in immediate hypersensitivity reactions and also have pronounced inflammatory effects. Administration of the NSAIDs alone can produce allergic reactions including bronchospastic reactivity; skin rashes; syndrome of abdominal pain, fever, chills, nausea and vomiting; and anaphylaxis. For this reason, aspirin and the other non-steroidal anti-inflammatory agents (NSAIDs) are generally contraindicated for patients suffering from asthma or who have previously exhibited allergic sensitivity to aspirin or other NSAIDs.

Prior to the recognition of the significance of the 5-lipoxygenase pathway of arachidonic acid metabolism in allergic reactions and inflammation, the search for effective therapeutic agents was based primarily on those agents which treated the symptoms of allergy and inflammation. There has since been effort to develop new drugs which selectively block the formation of the mediators of these conditions, and the present invention provides new chemical entities which are inhibitors of the 5-lipoxygenase and/or cyclooxygenase pathway and are useful in the treatment of asthma, rheumatoid arthritis, psoriasis, and other allergic, hypersensitivity, and inflammatory conditions. In addition, those compounds which stimulate superoxide generation may be useful in the adjunctive therapy of microbial infections.

See Goodman and Gilman's, The Pharmacological Basis of Therapeutics (7th Edition, 1985) p. 660–673; P. A. Ward, et. al., "Oxygen Radicals, Inflammation and Tissue Injury," FREE RADICAL BIOLOGY & MEDICINE, 5: 403–408 (1988); and C. E. Cross, et. al., "Oxygen Radicals and Human Disease," ANN. INT. MED., 107: 526–545 (1987).

The present invention provides compounds which block the 5-lipoxygenase metabolic pathway and, therefore, block the formation of the leukotrienes responsible for allergy and inflammation, and represent therapeutic agents which are useful in the treatment of allergic and hypersensitivity reactions and inflammation, alone, or also may be utilized in combination with other lipoxygenase inhibitors or with cyclooxygenase inhibitors such as the non-steroidal anti-inflammatory agents.

Recently, oxygen radicals have been implicated in the pathogenesis of many diseases. This implication is reflected by the many conferences devoted to this topic, books on the subject of free radicals and disease, and the appearance of two new specialized journals: *Free Radical Research Communications*, and *Free Radical Biology and Medicine*.

Much is known about the physicochemical properties of the various oxygen radicals, but knowledge of their overall importance in the initiation and amplification of human disease is limited. Some clinical conditions in which oxygen radicals are thought to be involved are discussed in Cross, C. E., et al., "Oxygen Radicals and Human Disease," ANN. INT. MED., 107:526–545 (1987) (see Table 1, p. 527) and Ward, P. A., et al., "Oxygen Radicals, Inflammation, and Tissue Injury," FREE RADICAL BIOLOGY & MEDICINE, 5:403–408 (1988). Among the clinical conditions in which oxygen radicals are thought to be involved are, for example, inflammatory-immune injury, autoimmune diseases, ischemia-reflow states, aging disorders, cancer, cigarette-smoke effects, emphysema, acute respiratory distress syndrome (ARDS), atherosclerosis, rheumatoid arthritis, senile dementia, cataractogenesis, retinopathy of prematurity, and contact dermatitis.

Oxygen radicals are capable of reversibly or irreversibly damaging compounds of all biochemical classes, including nucleic acids, protein and free amino acids, lipids and lipoproteins, carbohydrates, and connective tissue macromolecules. These species may have an impact on such cell activities as membrane function, metabolism, and gene expression. Oxygen radicals are formed in tissues by many processes (see Cross, et al., p. 528, Table 2). These are believed to be both endogenous, such as mitochondrial, microsomal and chloroplast electron transport chains; oxidant enzymes such as xanthine oxidase, indoleamine dioxygenase, tryptophan dioxygenase, galactose oxidase, cyclooxygenase, lipoxygenase, and monoamine oxidase; phagocytic cells such as neutrophils, monocytes and macrophages, cosinophils, and endothelial cells; and antioxidation reactions; and exogenous, such as redox-cycling substances, drug oxidations, cigarette smoke, ionizing radiation, sunlight, heat shock and substances that oxidize glutathione. They may be involved in the action of toxins such as paraquat, cigarette smoke, and quinone antitumor drugs.

Generation of reactive oxygen species is a critical event in successful host defense against invading organisms. Both neutrophils and macrophages rely on a variety of oxidants to damage bacterial constituents (see V. L. Shepherd, "The role of the respiratory burst of phagocytes in host defense," SEMIN. RESPIR. INFECT. (United States) June 1986, 1(2) p. 99–106).

Various thioether compounds have been described previously. For example, U.S. Pat. No. 4,711,903 and its continuation-in-part, U.S. Pat. No. 4,755,524 disclose compounds of the formula

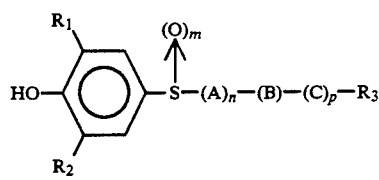

wherein: $R_1$ and $R_2$ are the same or different and independently represent tert-alkyl or phenyl; A represents methylene or methylene substituted by alkyl, dialkyl or hydroxy, provided that when A includes hydroxymethylene, the hydroxymethylene group is not adjacent to a heteroatom; B represents sulfur, sulfoxide, sulfone, oxygen, —NH— or nitrogen substituted by alkyl, phenyl, benzyl, substituted phenyl or substituted benzyl; C represents methylene or methylene substituted by alkyl; $R_3$ represents $CO_2H$, $CO_2$-alkyl or a tetrazole group; m is 0 or 1, n is 2, 3 or 4 and p is 1, 2 or 3; and the pharmaceutically acceptable salts thereof. The compounds are specific inhibitors of 5-lipoxygenase and are useful in the treatment of local and systematic inflammation, allergy and hypersensitivity reactions and other disorders in which agents formed in the 5-lipoxygenase metabolic pathway are involved.

European Patent Application Publication No. 0131221 discloses compounds of the formula:

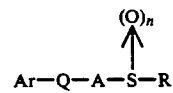

in which Ar is phenyl or phenyl substituted by one to three of varied substituents, for example, alkyl, alkoxy, hydroxy, etc.; Q is oxygen, sulfur or an NH group; A is straight or branched chain, optionally substituted, alkylene and R is hydrogen or straight or branched alkyl, optionally substituted by alkoxy, hydroxyl, carboxyl, alkoxycarbonyl, etc.; and n is 0, 1 or 2. The disclosed compounds are indicated to have anti-inflammatory and anti-allergic properties through inhibition of undefined anaphylactic and anaphylactoid reactions, although no test data are provided. The preferred compounds are stated to be those in which Q represents oxygen and n is 0 without mention of any preference among the numerous possible substituents for R or substituted phenyl as Ar. In contrast to the invention disclosed in the foregoing publication, the compounds of the present invention all have a sulfur atom at the position corresponding to Q as well as having di(tertiary)-alkyl or diphenyl groups as substituents on the phenol moiety corresponding to the substituted Ar group in the above publication which, as described therein, may or may not comprise a phenol. Moreover, it is noted that the compounds of the present invention have been found to possess specificity for the inhibition of 5-lipoxygenase which is an important distinctive property not attributed to the compounds in the foregoing publication. Those of ordinary skill in the art will appreciate that the compounds of formula I of this invention, including their surprising specific 5-lipoxygenase inhibitory properties, are, therefore, not specifically described in the aforementioned EPA publication No. 0131221.

U.S. Pat. Nos. 4,029,812, 4,076,841 and 4,078,084 disclose compounds of the formula

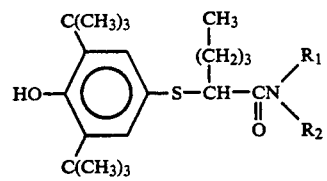

comprising 2-(3,5-di-tert -butyl-4-hydroxy-phenyl) thio carboxamides. The compounds are indicated to be useful in lowering plasma lipid levels including serum cholesterol and triglyceride levels.

U.S. Pat. No. 4,153,803 discloses cholesterol-lowering phenoxyalkanoic acid esters of the formula

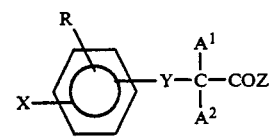

wherein, when Y is sulfur, X is hydrogen, benzyl, benzyloxy or benzylthio or substituted derivatives thereof;

R is hydrogen, halogen, hydroxy, alkyl or alkoxy, $A^1$ and $A^2$ are hydrogen or alkyl and Z is amine or azacyclohydrocarbonyloxy.

U.S. Pat. No. 4,663,333 discloses compounds of the formula

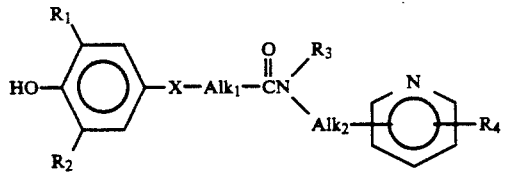

wherein: $R_1$ and $R_2$ are the same or different members of the group consisting of halo, phenyl, substituted phenyl and a

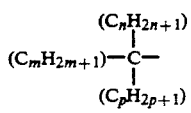

group wherein n, m and p are independently an integer of from 1 to 8 provided $n+m+p$ is equal to or less than 10; X is thio, sulfinyl or sulfonyl; $Alk_1$ is straight or branched chain lower alkylene of 1 to 6 carbon atoms, $R_3$ is lower alkyl, $Alk_2$ is straight or branched chain alkylene of 1 to 4 carbon atoms; $R_4$ is selected from the group consisting of hydrogen halo, hydroxy, lower alkyl and lower alkyxy; and the pharmaceutically acceptable salts there of. The compounds inhibit 5-lipoxygenase and are useful in the treatment of inflammation, allergy and hypersensitivity reactions and other disorders of the immune system. European Patent Application EP 0372409 published Jun. 13, 1990 discloses that these compounds are useful in inhibiting the invasive activity of tumor cells and the resulting metastasis.

European Patent Application EP 0190685 discloses heterocyclic amides represented by the formula

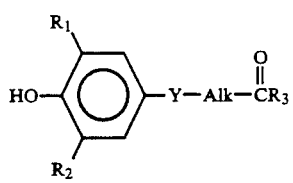

wherein $R_1$ and $R_2$ are the same or different members of the group consisting of halo, phenyl, substituted phenyl and a

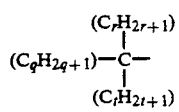

group wherein q, r and t are independently an integer of from 1 to 8 provided that $q+r+t$ is equal to or less than 10; Y is thio, sulfinyl or sulfonyl; Alk is straight or branched chain lower alkylene, and $R_3$ is a heterocyclic amine represented by the formula:

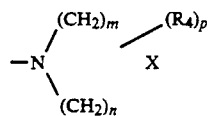

wherein $R_4$ is selected from the group consisting of hydrogen, lower alkyl, phenyl, substituted phenyl, benzyl, substituted benzyl, carboxyl or carboxyloweralkyl; X is selected from the group consisting of $N-R_4$, and $CH_2$; m is 2 or 3; n is 2 or 3 when X is O or $N-R_4$ and n is 1 to 3 when X is $CH_2$; p is 0 to 2; and the pharmaceutically acceptable salts thereof. The compounds inhibit 5-lipoxygenase and are useful as anti-inflammatory and anti-allergy agents. European Patent Application EP 0372410 published Jun. 13, 1990, discloses that these compounds are useful in inhibiting the invasive activity of tumor cells and the resulting metastasis.

European Patent Application EP 0190682 discloses anilides represented by the formula

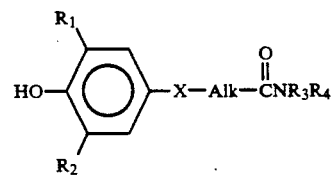

wherein: $R_1$ and $R_2$ are the same or different members of the group consisting of halo, phenyl, substituted phenyl and a

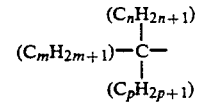

group wherein n, m and p are independently an integer of from 1 to 8 provided that $n+m+p$ is equal to or less than 10; X is thio, sulfinyl or sulfonyl; Alk is straight or branched chain lower alkylene; $R_3$ is hydrogen or lower alkyl; and $R_4$ is phenyl or substituted phenyl. The compounds inhibit 5-lipoxygenase and are useful in the treatment of allergy and hypersensitivity reactions and inflammation.

U.S. Pat. No. 4,857,558 discloses methods for inhibiting lipoxygenase and includes pharmaceutical formulations comprising a pharmaceutical carrier and an effective lipoxygenase inhibiting amount of a compound of the formula

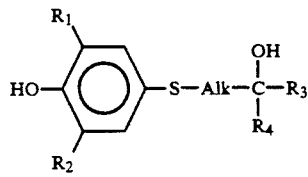

wherein: $R_1$ and $R_2$ are the same or different members of the group consisting of 1,1-dimethylethyl, halo, phenyl and substituted phenyl; Alk is straight or branched chain lower alkylene; $R_4$ is hydrogen or lower alkyl; $R_3$ is hydrogen or lower alkyl or a cycloalkyl group of from 3 to 8 carbon atoms. The disclosed compounds inhibit 5-lipoxygenase and are useful in the treatment of allergy and hypersensitivity reactions and inflammation.

United Kingdom Patent No. 1,557,622 discloses 3,5-di-tertiary-butyl-4-hydroxyphenyl pyridine compounds of the formula:

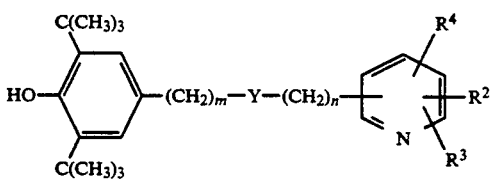

or a pharmaceutically acceptable acid addition salt thereof, wherein:

y is —O—, —S— or —N(R⁴)— [wherein R⁴ is a hydrogen atom, an alkyl group having 1 to 4 carbon atoms (e.g. methyl, ethyl, propyl or butyl), an aralkyl group (e.g. benzyl, methoxybenzyl or phenethyl)];

each of R¹ and R² is a hydrogen atom, a hydroxyl group or an alkyl group having 1 to 4 carbon atoms (e.g. methyl, ethyl, propyl or butyl);

R³ is a hydrogen atom, a hydroxymethyl group or a group of the formula:

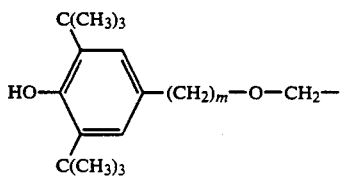

m is 0 or 1; and
n is 0, 1, 2 or 3.

Preferable compounds of the formula are those wherein Y is —O— or —N(R⁴)— (wherein R⁴ is as defined above). These compounds are said to have antiarterosclerotic, antihyperlipidemic, cerebral vasodilating and antithrombotic activities, and are useful as drugs for the treatment of eschemic vascular diseases in mammals such as artherosclerosis, cardiac infarction, angina pectoris, cerebral infarction, cerebral hemorrhage, renal infarction, intermittent claudication, transient cerebral attack or thrombosis.

German Offenlegunsschrift 1 936 463 discloses phenols having the formula

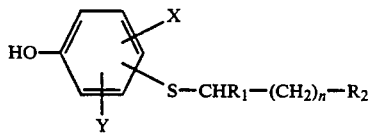

in which
X and Y, which may be the same or different, stand for hydrogen or halogen atoms or lower alkyl radicals,
R₁ stands for a hydrogen atom or a lower alkyl radical,
R₂ stands for one of the groups,

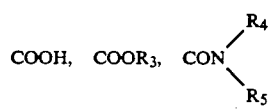

CN, and, in case n equal 0 and R₁ is a hydrogen, it can only be C₆H₅ and in case n equal 1, it can also be OH, whereby R₃ stands for an alkyl radical with 1 to 5 carbon atoms and R₄ and R₅, which may be the same or different, stand for hydrogen atoms, lower or medium alkyl radicals or, together with the nitrogen atom, stand for a ring that may contain another heteroatom,
n stands for 0 or 1 as well as with the corresponding phenolates. The phenols are said to have biocidal activity but they are said to be above all suitable as intermediates for the preparation of biocidal substances, for example, phosphate esters and carbamates.

SUMMARY OF THE INVENTION

The present invention relates to compounds of the Formula I

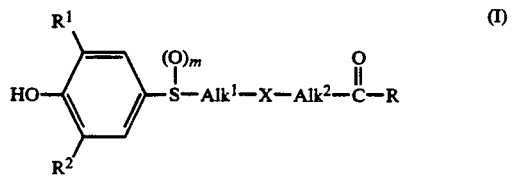

wherein R¹ and R² are the same or different and independently represent tert-alkyl or phenyl; Alk¹ represents straight or branched chain alkylene of 1 to 10 carbon atoms; X represents sulfur or oxygen; Alk² represents straight or branched chain alkylene of 1 to 4 carbon atoms; m is 0, 1 or 2; and R represents

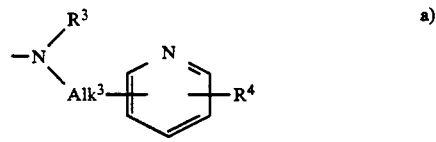

wherein R³ is hydrogen or alkyl of 1 to 4 carbon atoms; Alk³ is straight or branched chain alkylene of 1 to 4 carbon atoms; and R⁴ is hydrogen or alkyl of 1 to 4 carbon atoms; or

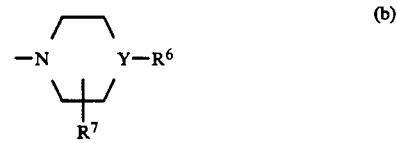

wherein Y is CH, N, O, or S; R⁶ is hydrogen, lower alkyl, phenyl, substituted phenyl, benzyl, substituted benzyl, or a heterocyclic amine and R⁷ is hydrogen or alkyl of 1 to 4 carbon atoms;
and the pharmaceutically acceptable salts and stereoisomers and geometric isomers thereof.

The compounds of formula I are inhibitors of 5-lipoxygenase and are useful in the treatment of allergies, inflammation, psoriasis, adult respiratory distress syndrome (ARDS) and hypersensitivity reactions and related disorders and conditions in which physiologically active agents formed in the 5-lipoxygenase metabolic pathway are involved.

Compounds of the present invention also affect superoxide generation. They may stimulate generation of superoxide, or in some cases they may operate in a biphasic manner, stimulating superoxide generation at lower doses and inhibiting superoxide generation at higher doses. Thus, they may also be used to modulate superoxide generation.

The compounds of Formula I which act as stimulators of superoxide generation may be useful in the therapeutic or prophylactic treatment of disease conditions in which superoxide generation is an important factor.

The compounds of Formula I which are inhibitors of superoxide generation at certain doses may be useful in the therapeutic or prophylactic treatment of disease conditions which are mediated wholly or partly by superoxide generation such as adult respiratory distress syndrome, superoxide mediated inflammatory or allergic conditions, and other medical conditions which are caused by or aggravated by superoxide.

Although it has been speculated that 5-lipoxygenase may be involved in superoxide generation, the ability of these compounds, which inhibit 5-lipoxygenase, to stimulate superoxide generation in neutrophils indicates that superoxide generation is not governed by 5-lipoxygenase. Thus the activity of the compounds of Formula I in stimulating superoxide generation is not related to the ability to inhibit 5-lipoxygenase.

The present invention also provides a method by which neutrophil activation and the generation of superoxide anions are accomplished utilizing the compounds of formula I. Accordingly the compounds of formula I are useful in the design and testing of anti-inflammatory properties of other pharmacologically active agents.

The ability to produce superoxide which may itself be microbicidal or which is then converted to toxic oxidants such as $H_2O_2$, $\cdot OH$, and singlet oxygen is important to the phagocytic killing mechanisms which enable neutrophils and macrophages to kill bacteria and parasites through phagocytosis.

Therefore, compounds of formula I which stimulate superoxide generation may be useful in the adjunctive therapy of microbial infections. The compounds may also be useful in treating conditions such as Chediak-Higashi Syndrome in which the patient's macrophages and polymorphs are only weakly active causing the patients to suffer from recurring infections involving organisms with normally low pathogenicity. Compounds of formula I may also be useful in the adjunctive therapy of patients whose immune systems have been weakened or impaired by disease or by chemotherapy or radiation therapy and who are more subject to microbial infections.

DETAILED DESCRIPTION OF THE INVENTION

Preferred compounds of the present invention are compounds of the formula

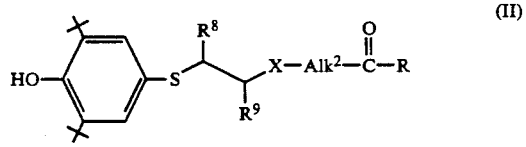

(II)

and the pharmaceutically acceptable salts and stereoisomers and geometric isomers thereof, wherein $R^8$ and $R^9$ are alike or different and are hydrogen or alkyl of 1 to 4 carbon atoms; and R is defined as hereinbefore.

The term "tert-alkyl" as used herein in reference to $R_1$ and $R_2$ refers to branched chain alkyl moieties of from about 4 to 10 carbon atoms having a tertiary carbon atom attached to the phenyl ring substituted by $R_1$ and $R_2$. Examples of such groups are tert-butyl, i.e., 1,1-dimethylethyl, 1-1-dimethylpropyl, 1-methyl-1-(ethyl)pentyl, 1,1-diethylpropyl, 1-ethyl-1-(propyl)butyl and the like.

The term "alkylene" refers to straight or branched chain alkylene groups having between about 1 to 10 carbon atoms including, for example, methylene, ethylene, propylene, 1,2-dimethylethylene, pentylene, 1-methylbutylene, isopentylene, neopentylene, etc.

The term "lower alkyl", as used herein, refers to straight or branched chain alkyl groups having from 1 to 6 carbon atoms, inclusive, i.e., methyl, ethyl, n-propyl, iso-propyl, n-butyl, sec-butyl, tert-butyl, n-pentyl, 2-methylbutyl, 2,2-dimethylbutyl, n-hexyl, and the like.

The terms "substituted phenyl" and "substituted benzyl" refers to phenyl or benzyl having one or more substituents selected from the group consisting of halo, hydroxy, lower alkyl, acyl, and lower alkoxy.

Particularly preferred compounds of Formula I are those wherein $R_1$ and $R_2$ are both tert-alkyl.

The term heterocyclic amine refers to a 5 to 7 membered heterocyclic ring containing one or two heteroatoms and includes piperidine, piperazine, pyridine, morpholine and thiomorpholine and the like.

The expression "pharmaceutically acceptable salts" is intended to include those salts capable of being formed with the compounds of the present invention without materially altering the chemical structure or pharmacological properties thereof. Such salts include but are not limited to inorganic and organic cations or acid addition salts, such as sodium, potassium, calcium, ammonium, alkylammonium, triethanolamine, lysine, hydrochloric, hydrobromide, citrate, tosylate, etc. well known to those skilled in the art. The foregoing salts are prepared in the conventional manner by neutralization of the compounds of Formula I with the desired base or acid.

The compounds of the present invention can be administered in such oral dosage forms as tablets, capsules, pills, powders, granules, elixirs, or syrups as well as aerosols for inhalation. Likewise, administration may be effected intravascularly, subcutaneously, or intramuscularly using dosage forms known to those of ordinary skill in the pharmaceutical arts. In general, the preferred form of administration is oral. An effective but non-toxic amount of the compound is employed in treatment. The dosage regimen utilizing the present compounds is selected in accordance with a variety of factors including the type, age, weight, sex, and medical condition of the patient; the severity of the condition to be ameliorated; and the route of administration. A physician of ordinary skill can readily determine and prescribe the effective amount of the drug required to prevent, treat or arrest the progress of the particular condition. For modulating superoxide generation, the effective amount for administration is ordinarily that amount which is required to assure that the mammalian neutrophils involved in the generation of superoxide will be exposed to a sufficient concentration of drug to stimulate or inhibit the generation of superoxide. A dosage regimen can be effectively determined for each patient or animal by initial intravenous infusion at a low dosage level, e.g., 0.01 µg/kg/min and thereafter increasing the dosage until the desired effect is obtained. Thereafter, oral dosages can be determined which will yield equivalent blood levels of drug. Dosages of the compounds of the present invention, will range generally between about 0.1 mg/kg/day to about 100 mg/kg/day and preferably between about 0.5 mg/kg/day to about 50 mg/kg/day when administered to patients suffering from allergic or hypersensitivity reactions or inflammation. The compounds may also be administered transdermally or topically. The daily dosage may be administered in a single dose or in equal divided doses three or four times daily.

In the pharmaceutical compositions and methods of the present invention, at least one of the active compounds of the invention or a pharmaceutically acceptable salt thereof will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug component may be combined with any oral non-toxic pharmaceutically acceptable inert carrier such as lactose, starch, sucrose, cellulose, magnesium stearate, dicalcium phosphate, calcium sulfate, mannitol and the like; for oral administration in liquid form, the active drug component may be combined with any oral non-toxic pharmaceutically acceptable inert carrier such as ethanol and the like. Moreover, when desired or necessary, suitable binders, lubricants, disintegrating agents and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes. Lubricants for use in these dosage forms include boric acid, sodium benzoate, sodium acetate, sodium chloride, and the like. Disintegrators include, without limitation, starch, methylcellulose, agar, bentonite, guar gum, and the like.

BIOLOGICAL EVALUATIONS

The compounds of the invention are evaluated with respect to 5-lipoxygenase inhibition according to the following assay procedure.

Inhibition of 5-lipoxygenase, in vitro: anti-inflammatory, anti-allergy activities.

The 100,000× g supernatant fraction of Rat Basophilic Leukemia Cell Homogenate (RBL-1) serves as a 5-lipoxygenase enzyme source. The enzyme is incubated with [1-$^{14}$C)-arachidonic acid and Ca++ in the presence and absence of test compound. The product of 5-lipoxygenase, 5-hydroxyeicosatetraenoic acid (5-HETE), is separated by thin-layer chromatography and measured by radioactivity. A compound inhibiting 5-HETE synthesis by 30% or more is considered active at that concentration. Initial screening doses are $1 \times 10^{-4}$M. When the compound inhibits more than 50% of 5-HETE synthesis at $10^{-4}$M, that compound is tested at multiple dose levels to determine the IC$_{50}$ value (inhibitory concentration to inhibit 50%).

The compounds of the invention are evaluated with respect to superoxide modulating activity according to the following assay procedure:

Human neutrophil superoxide generation: Superoxide generation by formyl-methionyl-leucyl-phenylalanine (FMLP)-stimulated neutrophils was quantitated by the reduction of cytochrome C (Badwey, J. A., Curnutte, J. T. and Karnovsky, M. L., cis-Polyunsaturated fatty acids induce high levels of superoxide production by human neutrophils. J. Biol. Chem. 256: 12640-12643, 1981.) To 5 million neutrophils in 2.85 ml of Krebs-Ringer phosphate buffer, pH 7.2, 50 ul of inhibitor (in 10% DMSO/buffer), and 50 ul ferricytochrome C (5 mM, stock) were added and preincubated for 3 minutes at 37° C. Absorption measurements at 550 nm were recorded at start of preincubation. Fifty ul FMLP (6 uM, stock) was added to initiate reaction. A plateau was reached within 3 minutes and this reading—initial reading (before addition of FMLP) was used to calculate nanomoles of superoxide generated based on a molar extinction coefficient of $2.1 \times 10^4$ cm$^{-1}$mole$^{-1}$.

Isolation of human neutrophils: Human neutrophils were isolated from freshly drawn blood of healthy donors. Two ml of 5% dextran (MW 200,000-300,000) in saline was added to 10 ml aliquots of blood, mixed and placed upright for 45 min. at 37° C. Approx. 8-10 ml of the plasma-white cell suspension from the dextran sedimentation was layered on 3 ml of Ficol-paque in a 15 ml tube and centrifuged at 400 g for 30 min. The supernate, containing plasma and platelets, was discarded by aspiration, and the pellet, containing predominantly neutrophils, was resuspended in 1 ml saline. The suspension was transferred to a clean tube, and pooled with other aliquots of blood treated similarly. The pooled suspension was centrifuged at 350 g for 5 min. and supernate discarded. The pellet was resuspended in 5 ml of 0.05% NaCl with a plastic Pasteur pipette for 25 seconds to lyse contaminating red cells, then 5 ml of 1.75% NaCl added to regain isotonicity. The red cell lysing procedure was repeated, the cells suspended in appropriate buffer (depending on assay) and counted.

For comparison the compound of Formula IV, a known 5-lipoxygenase inhibitor described in U.S. Pat. No. 4,755,524 was used.

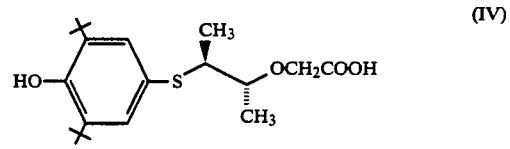
(IV)

The results with respect to certain compounds of the present invention are set forth in Table I below.

TABLE 1

| Compound Example Number | 5-Lipoxygenase Inhibition IC$_{50}$ (μM) | Effect on FMLP Induced Superoxide |
|---|---|---|
| 13 | 0.16 | Stimulated at 1–50 μM (171% > control) |
| 14 | 0.22 | a) Stimulated at 1–10 μM (171% > control) b) Inhibited at 25–50 μM (57% < control) |
| 15 | 0.13 | a) Stimulated at 1–10 μM (38% > control) b) Inhibited at 50 μM (13% < control) |
| 16 | 0.16 | a) Stimulated at 1–50 μM (146% > control) b) Inhibited at 50 μM (13% < control) |
| 17 | 0.20 | Stimulated at 1–50 μM (60% > control) |
| 19 | 0.46 | Stimulated at 1–50 μM (33% > control) |
| 20 | 0.40 | a) Stimulated at 1–25 μM (135% > control) b) Inhibited at 50 μM (100% < control) |
| 21 | 0.15 | Stimulated at 50 μM (46% > control) |
| 22 | 0.17 | Stimulated at 50 μM |

TABLE 1-continued

| Compound Example Number | 5-Lipoxygenase Inhibition IC$_{50}$ (µM) | Effect on FMLP Induced Superoxide |
|---|---|---|
| Formula IV | 4.9 | (17% > control) Inhibited superoxide generation; IC$_{50}$ = 11 µM |

Unlike the compounds of the present invention which stimulated superoxide generation or acted biphasically to stimulate superoxide generation at lower doses and inhibit superoxide generation at higher doses, the compound of Formula IV inhibited both superoxide generation and 5-lipoxygenase. This data indicates that superoxide generation is not dependent on 5-lipoxygenase and that the ability of a compound to inhibit 5-lipoxygenase is not related to its ability to simulate superoxide generation.

The following non-limiting examples further illustrate details for the preparation of the compounds used in practicing the present invention. Those skilled in the art will readily understand and appreciate that known variations of the conditions and procedures in the following preparative methods can be utilized. All temperatures are degrees Celsius unless otherwise noted. Melting points were determined on a Thomas-Hoover melting point apparatus and are uncorrected.

The compounds of the present invention can be prepared from the corresponding acids as shown in Scheme A by first reacting the acid (III) with an appropriate chloride to give the acid chloride (IIIa) and then reacting the acid chloride with an appropriate amine RH to produce the amides of formula I.

SCHEME A

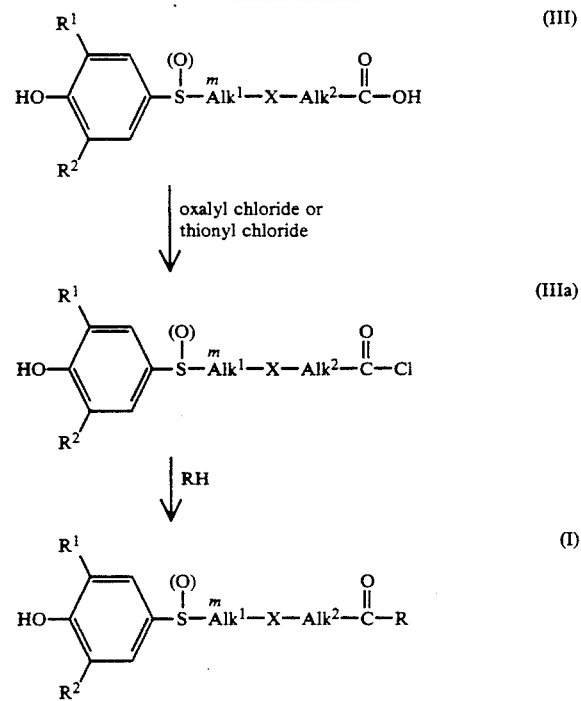

EXAMPLE 1

3,5-bis(1,1-dimethylethyl)-4-hydroxyphenyl thiocyanate

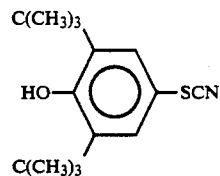

To a three-necked, round bottom 5 L flask, equipped with a mechanical stirrer, gas inlet, thermometer and gas outlet, was added 2,6-di-tert-butylphenol (474 g, 2.30 mole), ammonium thiocyanate (76.12 g, 4.83 mole) and methanol (1200 ml). The reaction mixture was stirred and cooled to 0° C. in an ice/salt bath. Maintaining the temperature at 0° to 10° C., chlorine gas was slowly bubbled through the mixture for about 1 hour whereupon the reaction mixture was a heterogeneous yellow color. Ammonia was then bubbled through the reaction for about 1 and ½ hours, maintaining the reaction mixture at a temperature of between 0° to 10° C. The reaction was stirred for an additional hour at 0° C., poured into 2 L of cold distilled water and refrigerated overnight. The aqueous phase was decanted and the solid taken up in methanol, precipitated by addition of water, filtered and dried for 2 days over phosphorous pentoxide. The resulting gummy yellow solid was recrystallized from pentane and dried in vacuo to yield the product as a white powder, m.p. 61.5°–63° C.

Analysis calc. for $C_{14}H_{21}NSO$: Theory: C, 68.40; H, 9.03; N, 5.32; S, 12.17. Found: C, 68.85; H, 8.05; N, 5.29; S, 12.12.

EXAMPLE 2

2,6-bis(1,1-dimethylethyl)-4-mercaptophenol

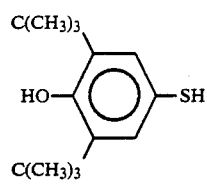

3,5-bis(1,1-Dimethylethyl)-4-hydroxyphenyl thiocyanate (55 g, 0.209 mole) was dissolved in acetone (200 ml) under an argon atmosphere. Water (7.6 g, 0.42 mole) was added and the reaction cooled to 0° C. Triethylphosphine (24.7 g, 0.209 mole) was added dropwise over a period of 1 hour and the reaction was then allowed to warm to room temperature with stirring. The solution was concentrated, solvents removed, and the resulting oil purified by chromatography on silica. The fractions containing the thiol were combined, the solvents removed to yield a white powder which was recrystallized from methanol/water and dried to yield 43.3 g of the desired product. NMR confirmed the identity of the product.

EXAMPLE 3

[[2-[[3,5-bis(1,1-dimethylethyl)-4-hydroxyphenyl]thio]ethyl]thio]acetic acid, monosodium salt

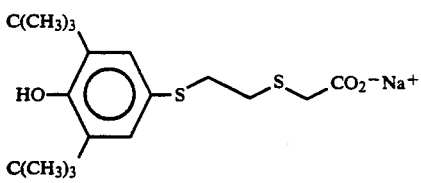

Mercaptoacetic acid (1.3 g, 0.0144 mole) was added to a solution of sodium ethoxide, prepared from sodium (0.66 g, 0.0288 mole) in ethyl alcohol (25 ml). After stirring for one hour, 1-bromo-2-chloroethane (6 ml, 0.072 mole) was added all at once and the solution stirred for 2 hours. After refluxing for 4 hours, the excess 1-bromo-2-chloroethane was removed by rotary evaporator. Ethyl alcohol (50 ml) was added to the residue and the sodium salt of 2,6-bis(1,1-dimethylethyl)-4-mercaptophenol prepared form sodium (0.33 g, 0.0144 mole) and 2,6-bis(1,1-dimethylethyl)-4-mercaptophenol (3.43 g, 0.0144 mole) in ethyl alcohol (25 ml) was added by cannula. After stirring for eighteen hours at room temperature, the mixture was refluxed for 1 hour, cooled to room temperature and water (50 ml) added with rapid stirring. The ethyl alcohol was removed with a rotary evaporator. The aqueous residue was extracted with ethyl acetate (2×100 ml) combined, dried over sodium sulfate, filtered and concentrated. The residue was crystallized from ethyl acetate/hexane. This solid was recrystallized from ethyl acetate/hexane to give the title compound.

Analysis calc. for $C_{18}H_{27}O_3S_2Na$ (378.54): Calc.: C, 57.11; H, 7.19; S, 16.94. Found: C, 56.75; H, 7.24; S, 16.84.

EXAMPLE 4

[[2,[[3,5-bis(1,1-dimethylethyl)-4-hydroxyphenyl]thio]ethyl]thio]acetic acid

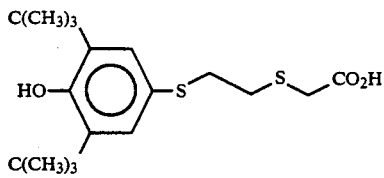

The title compound of Example 3 (0.90 g) was dissolved in water (40 ml) acidified with 10% hydrochloric acid and extracted into ethyl acetate (2×50 ml). The combined extracts were dried over sodium sulfate, filtered and concentrated using a rotary evaporator to give an oil. The oil was crystallized from hexane to give the title compound, m.p. ca. 86° C.

Analysis calc. for $C_{18}H_{28}O_3S_2$ (356.54): Calc: C, 60.64; H, 7.92; S, 17.98. Found: C, 60.93; H, 7.87; S, 17.81.

EXAMPLE 5

The title compound of Example 4 was also prepared by the procedure of Example 3 without the isolation of the sodium salt. The ethyl acetate solution containing the sodium salt was treated with ten percent hydrochloric acid, stirred for thirty minutes and the layers were separated. The organic layer was dried over sodium sulfate, filtered and concentrated with a rotary evaporator to give a solid which was recrystallized from hexane.

Analysis calc. for $C_{18}H_{28}O_3S_2$ (356.54): Calc: C, 60.64; H, 7.92; S, 17.98. Found: C, 60.73; H, 7.84; S, 17.92.

EXAMPLE 6

3-[[2-[[3,5-bis(1,1-dimethylethyl)-4-hydroxyphenyl]thio]ethyl]thio]propanoic acid

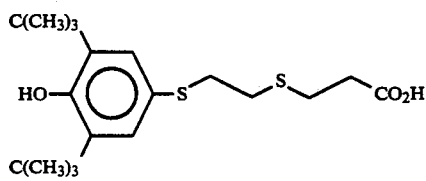

The title compound was prepared according to the method of Example 5 from 3-mercaptopropionic acid (6.1 g, 0.057 mole); sodium (3.9 g 0.17 mole); 1-bromo-2-chloroethane (12.4 g, 0.086 mole); and 2,6-bis(1,1-dimethylethyl)-4-mercaptophenol (13.7 g, 0.057 mole), purified by chromatography on silica and recrystallized from ethyl acetate/hexane, m.p. ca. 57.5° C.

Analysis calc. for $C_{19}H_{30}O_3S_2$ (370.6): Calc: C, 61.58; H, 8.16; S, 17.30. Found: C, 61.64; H, 7.89; S, 17.32.

EXAMPLE 7

2,6-bis(1,1-dimethylethyl)-4-[(2-hydroxy-1-methylpropyl)thio]phenol

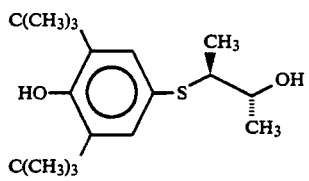

2,6-bis(1,1-Dimethylethyl)-4-mercaptophenol (18.2 g, 0.076 mole) was added to a solution of sodium ethoxide freshly prepared from sodium (3.5 g, 0.15 mole) in ethyl alcohol (100 ml) and stirred for 1 hour. After cooling to 5° C. with an ice bath, trans-2,3-epoxybutane (5.0 g, 0.069 mole) was added and the ice bath removed. After stirring for 5.5 hours the reaction mixture was poured into ten percent hydrochloric acid (50 ml). The ethyl alcohol was removed using a rotary evaporator and the aqueous residue extracted with ethyl acetate (2×75 ml). The extracts were combined, dried over sodium sulfate, filtered, and concentrated to an orange oil. The product was purified by chromatography on silica to give a yellow solid which was recrystallized from hexane to give a white solid, m.p. ca. 73° C.

Analysis calc. for $C_{18}H_{30}O_2S$ (310.5): Calc: C, 69.63; H, 9.74; S, 10.33. Found: C, 69.75; H, 9.60; S, 10.35.

EXAMPLE 8 methyl[[2-[[3,5-bis(1,1-dimethylethyl)-4-hydroxyphenyl]thio]-1-methylpropyl]thio]acetate

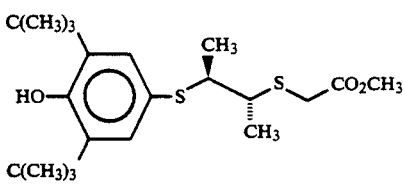

The title compound of Example 7 (3.5 g, 0.0112 mole) was added to trifluoroacetic acid (4 ml) and stirred for one hour. The methyl thioglycolate (1 ml, 0.0112 mole) was added, the reaction stirred for 2.5 hours and then poured into water (100 ml) and ethyl acetate (25 ml). After 18 hours the layers were separated and the organic layer concentrated to give 5.6 g of an oil. The product was purified by chromatography on silica.

Analysis calc. for $C_{21}H_{34}O_3S_2$ (398.1): Calc: C, 63.28; H, 8.60; S, 16.09. Found: C, 63.17; H, 8.70; S, 16.15.

EXAMPLE 9

[[2-[[3,5-bis(1,1-dimethylethyl)-4-hydroxyphenyl]thio]-1-methylpropyl]thio]acetic acid

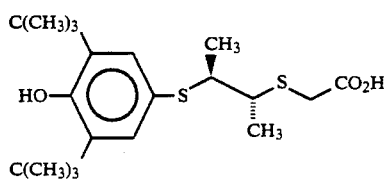

Lithium hydroxide monohydrate (0.20 g, 0.0035 mole) was added to a solution of the title compound of Example 8 (1.16 g, 0.0029 mole) in methyl alcohol (35 ml) and water (10 ml). When the reaction became clear more water was added. The reaction was acidified with ten percent hydrochloric acid. The methyl alcohol was removed using a rotary evaporator and the residue extracted with ethyl acetate. The ethyl acetate extract was dried over sodium sulfate, filtered and concentrated. The product was purified by chromatography on silica.

Analysis calc. for $C_{20}H_{32}O_3S_2$ (384.6): Calc: C, 62.46; H, 8.39; S, 16.67. Found: C, 62.33; H, 8.22; S, 16.37.

EXAMPLE 10

2,6-bis(1,1-dimethylethyl)-4-[(2-hydroxyethyl)thio]phenol

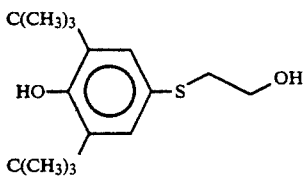

Triethylamine (0.42 g, 0.0042 mole), 2-bromoethanol (0.52 g, 0.0044 mole) and the title compound of Example 2 (1.0 g, 0.0042 mole) were stirred in methylene chloride (50 ml) for 20 hours. The reaction was condensed and ethyl acetate (25 ml) added to the residue. After filtering the white solid the filtrate was concentrated and the product purified by chromatography on silica, m.p. ca. 66° C.

Analysis calc. for $C_{16}H_{26}O_2S$ (282.4): Calc: C, 68.04; H, 9.28; S, 11.35. Found: C, 67.98; H, 9.20; S, 11.24.

EXAMPLE 11

[2-[[3,5-bis(1,1-dimethylethyl)-4-hydroxyphenyl]thio]ethoxy]acetic acid

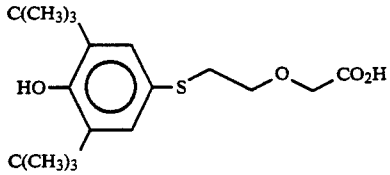

Chloroacetic acid (1.88 g) was added to a solution of the product of Example 10 (5.64 g) in tert. butyl alcohol. Potassium tert-butoxide (8.96 g) was added and the mixture refluxed for 22 hours. The reaction was made basic with 5% sodium bicarbonate and extracted with ethyl ether (3×50 ml). The $NaHCO_3$ extracts were acidified to about pH2 with 1N HCl and extracted 3 times with ethyl ether (100 ml). The combined organic extracts were washed twice with water, twice with saturated brine, dried over sodium sulfate and the solvent removed using a rotary evaporator to give the impure product. The product was purified by chromatography on silica, m.p. ca. 86° C.

Analysis calc. for $C_{18}H_{28}O_4S$ (340.47): Calc: C, 63.50; H, 8.29; S, 9.42. Found: C, 63.52; H, 8.02; S, 9.46.

EXAMPLE 12

(±)[2S*-[[3,5-bis(1,1-dimethylethyl)-4-hydroxyphenyl]thio]-1R*-methylpropoxy]acetic acid

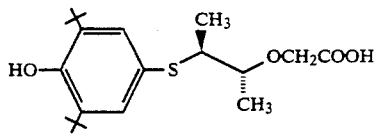

(a) Starting with the 2,6-bis(1,1-dimethylethyl)-4-[(2-hydroxy-1-methylpropyl)thio]phenol of Example 7 and using the method of Example 11 gave the title compound, m.p.ca. 89°-92° C.; Mass Spec. 368 (M+).

(b) In an alternate method a dry, argon purged vessel was charged with 1.6 kg of sodium hydride (60% dispersion in oil) which was then washed three times with a total of 21 kg of n-heptane. The reaction vessel was cooled to −20° C., and 41 L of dry tetrahydrofuran (THF) was added under argon. A solution of 4.0 kg of (±)2,6-bis(1,1-dimethylethyl)-4-[(2S*-hydroxy-1R*-methylpropyl)-thio]phenol in 16 L of tetrahydrofuran was added slowly to the sodium hydride suspension, and the mixture was warmed to 0°-5° C. and stirred for 1.5 h. The tetrahydrofuran was removed at reduced pressure, and 12 L of dimethyl sulfoxide was added under argon. A solution of 1.9 kg of sodium chloroacetate in 40 L of dimethyl sulfoxide was added, and the mixture was stirred at room temperature for approximately 15 h. When the reaction was complete, as indicated by thin layer chromatography, the reaction mixture was added to approximately 178 L of water at 5°-10° C., and the aqueous solution was extracted twice with a total of 60 L of n-heptane. The aqueous phase was acidified with 14 L of 4N hydrochloric acid and extracted three times with a total of 95 L of ethyl acetate. The combined organic phase was washed twice with a total of 74 L of water and once with 20 L of saturated aqueous sodium chloride solution. The organic phase was dried over 2.0 kg of anhydrous magnesium sulfate, filtered, and the solvent was removed by distillation under reduced pressure. The product was dissolved in 40 L of refluxing n-hexane, and the solution was cooled to room temperature. The product was collected by filtration, washed twice with a total of 20 L of n-hexane and dried at room temperature in a vacuum oven to give 4.27 kg (90% of theory) of (±)[2S*-[[3,5-bis(1,1-dimethyl-ethyl)-4-hydroxyphenyl]thio]-1R*-methylpropoxy]acetic acid (first crop). The hexane filtrate was concentrated under vacuum to give an additional 0.23 kg of product (4.80% of theory).

EXAMPLE 13

2-[[2-[3,5-bis(1,1-dimethylethyl)-4-hydroxyphenyl]thiolethyl]thio]-N-(2-pyridinylmethyl)acetamide

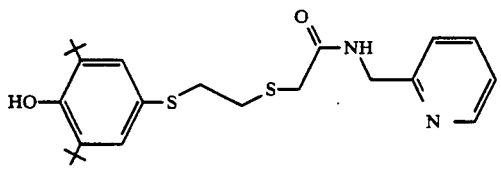

Oxalyl chloride (0.39 g, 0.0031 moles) was added by syringe to a solution of the title compound of Example 4 (1.0 g, 0.0028 moles) in benzene (50 ml) and stirred at room temperature for 20 hrs. The solution was concentrated by rotary evaporator under reduced pressure to an oil which was dissolved in tetrahydrofuran (50 ml). 2-(Aminomethyl) pyridine (0.30 g, 0.0028 moles) and triethylamine (0.5 ml) were both added and the solution was stirred for 4 days. Triethylamine hydrochloride was removed by filtration and the filtrate was concentrated by a rotary evaporator to an oil. The title compound was purified by silica gel chromatography. The structure assignment was supported by NMR, infrared spectra and elemental analysis (446.7).

Analysis calc. for $C_{24}H_{34}N_2O_2S_2$: C, 64.54; H, 7.67; N, 6.27. Found: C, 64.39; H, 7.58; N, 6.37.

EXAMPLE 14

(±)
2S*-[2-[[3,5-bis(1,1-dimethylethyl)-4-hydroxyphenyl]-thio]-1R*-methylpropoxy]-N-methyl-N-[2-(2-pyridinyl)ethyl]acetamide

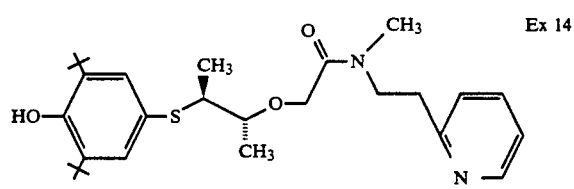

Ex 14

The title compound was prepared by the method of Example 13 by the substitution of Example 12 for Example 4 and 2-(2-methylamino ethyl)pyridine for 2-(Aminomethyl)pyridine. After silica gel chromatography the crude product was converted to the hydrochloride salt by adding hydrogen chloride gas to an ethyl ether solution. This solution was concentrated to an oil with a rotary evaporator. This oil was dissolved in water (10 ml). The solution was made basic with sodium hydrogen carbonate and extracted with ethyl acetate. The ethyl acetate solution was dried over anhydrous sodium sulfate, filtered and stripped on a rotary evaporator to an oil. Purification by silica gel chromatography afforded the title compound. The structure assignment was supported by mass spectrometry and elemental analysis (486.7).

Analysis calc. for $C_{28}H_{42}N_2O_3S$: C, 69.10; H, 8.70; N, 5.76. Found: C, 68.94; H, 8.48; N, 5.85.

EXAMPLE 15

2-[[2-[[3,5-bis(1,1-dimethylethyl)-4-hydroxyphenyl]thio]ethyl]thio]-N-(3-pyridinylmethyl)acetamide

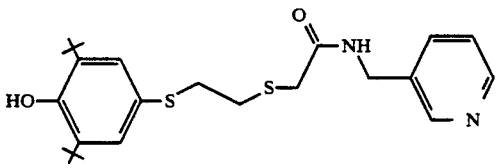

The title compound was prepared by the method of Example 13 by the substitution of 3-(aminomethyl)pyridine for 2-(aminomethyl)pyridine. Purification by silica gel chromatography afforded a solid which was recrystallized from ethyl acetate-hexane, DSC ca, 122° C. The structure assignment was supported by NMR, infrared spectra, mass spectroscopy and elemental analysis (446.7).

Analysis calc. for $C_{24}H_{34}N_2O_2S_2$: C, 64.54; H, 7.67; N, 6.27. Found: C, 64.44; H, 7.65; N, 6.28.

EXAMPLE 16

3-[[2-[[3,5-bis(1,1-dimethylethyl)-4-hydroxyphenyl]thio]ethyl]thio]-N-methyl-N-[2-(2-pyridinyl)ethyl]propanamide

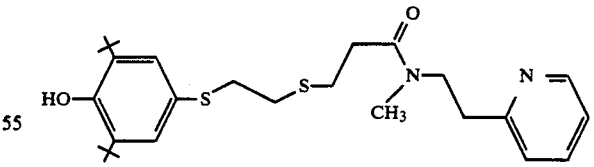

The title compound was prepared by the method of Example 13 by the substitution of Example 6 for Example 4 and 2-(2-methylamino ethyl)pyridine for 2-(aminomethyl)pyridine. The structure assignment was supported by NMR, infrared spectra and elemental analysis (488.8).

Analysis calc. for $C_{27}H_{40}N_2O_2S_2$: C, 66.35; H, 8.25; N, 5.73. Found: C, 66.25; H, 7.86; N, 5.69.

EXAMPLE 17

(±)
2S*-[[[2-[[3,5-bis(1,1-dimethylethyl)-4-hydroxyphenyl]-thio]-1R*-methylpropyl]thio]-N-(4-pyridinylmethyl-)acetamide

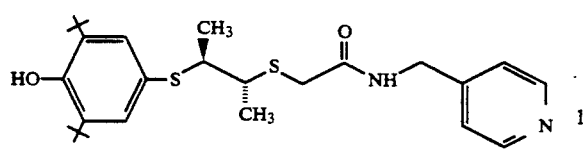

The title compound was prepared by the method of Example 13 by the substitution of Example 9 for Example 4 and 4-(aminomethyl)pyridine for 2-(aminomethyl)pyridine. The structure was supported by NMR, infrared spectra and elemental analysis (474.7).

Analysis calc. for $C_{26}H_{38}N_2O_2S_2$: C, 65.78; H, 8.07; N, 5.90. Found: C, 65.57; H, 7.83; N, 5.88.

EXAMPLE 18

1-[2-[2-[(3,5-bis(1,1-dimethylethyl)-4-hydroxyphenyl]-thio]ethoxy-1-oxoethyl]4]methylpiperazine

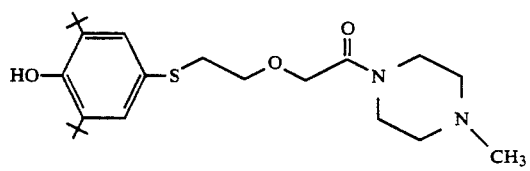

Oxalyl chloride (1.55 g, 0.0122 moles) was added to a cold (0° C.) solution of the title compound of Example 11 (0.50 g, 0.00148 moles) in benzene (5 ml). The reaction was stirred cold for 5 min. and at room temperature for an additional 40 min. and then concentrated to an oil with a gentle stream of nitrogen gas. The residue was dissolved in methylene chloride (5 ml). To this stirring solution was added N-methyl piperazine (0.163 g, 0.00148 moles) and triethylamine (0.2 ml, 0.00148 moles) and the reaction mixture was stirred overnight at room temperature. Water (5 ml) was added and the layers were separated. The organic layer was washed with water, dried over anhydrous magnesium sulfate and concentrated to an oil. The oil was purified by silica gel chromatography and recrystallized from hexane, DSC ca. 83° C. Structure assignment was supported by NMR, infrared spectra and elemental analysis (422.6).

Analysis calc. for $C_{23}H_{38}O_3N_2S$: C, 66.37; H, 9.06; N, 6.63; S, 7.59. Found: C, 65.53; H, 9.26; N, 6.59; S, 7.77.

EXAMPLE 19

(±)
1-[2-[2S*-[[3,5-bis(1,1-dimethylethyl)-4-hydroxyphenyl]thio]-1R*-methylpropoxy]-1-oxoethyl]-4-(phenylmethyl)piperazine

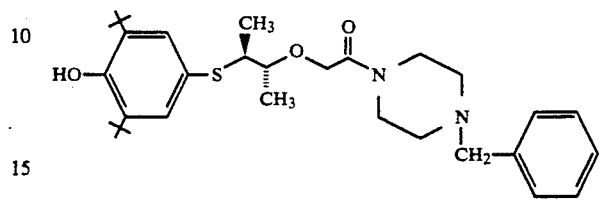

The title compound of Example 12 (1.0 g, 0.0027 moles) was added to thionyl chloride (0.6 ml, 0.0081 moles) and stirred at room temperature for 20 hrs. Toluene (50 ml) was added and the reaction concentrated by rotary evaporator at reduced pressure. The process was repeated with methylene chloride (50 ml). The residue was dissolved in methylene chloride (50 ml). With stirring, a solution of 1-benzylpiperazine (0.47 g, 0.0027 moles) in methylene chloride (10 ml) was added dropwise followed by triethylamine (2 ml). The solution was stirred at room temperature for 20 hrs., concentrated to an oil by a gentle stream of nitrogen. The residue was dissolved in ethyl acetate, filtered and concentrated by rotary evaporator under reduced pressure to an oil which was purified by silica gel chromatography. Structure assignment was supported by NMR, infrared spectra and mass spectrometry.

EXAMPLE 20

1-[2-[[2-[[3,5-bis(1,1-dimethylethyl)-4-hydroxyphenyl]-thio]ethyl]thio]-1-oxoethyl]-4-methylpiperazine

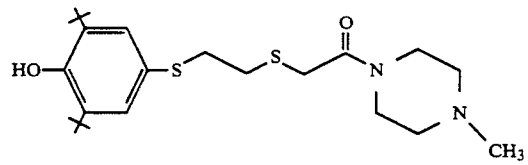

Oxalyl chloride (0.39 g, 0.0031 moles) was added by syringe to the title compound of Example 4 (1.0 g, 0.0028 moles) in benzene (50 ml) and the reaction mixture was stirred for 20 hrs. at room temperature. The reaction was concentrated under reduced pressure with a rotary evaporator to an oil which was dissolved in tetrahydrofuran (THF) (50 ml). A solution of 1-methyl piperazine (0.28 g, 0.0028 moles) in tetrahydrofuran (10 ml) was added dropwise followed by triethylamine (0.5 ml) and the resulting solution was stirred at room temperature for 20 hrs. The triethylamine hydrochloride was removed by filtration, and the solution was concentrated. The resulting oil was purified by silica gel chromatography. The structure assignment was supported by NMR, infrared spectra and elemental analysis (438.7).

Analysis calc. for $C_{23}H_{38}N_2O_2S_2$: C, 62.97; H, 8.73; N, 6.39. Found: C, 62.68; H, 8.45; N, 6.34.

EXAMPLE 21

1-[3-[[2-[[3,5-bis(1,1-dimethylethyl)-4-hydroxyphenyl]-thio]ethyl]thio]-1-oxopropyl]-4-(1-piperidinyl)piperidine

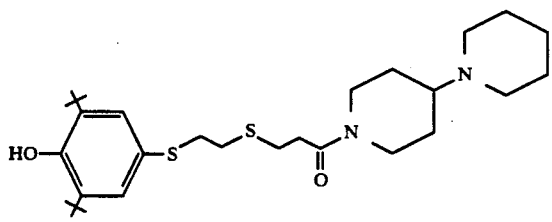

The title compound was prepared by the method of Example 20, substituting the compound of Example 6 for the compound of Example 4 and 4-piperidino piperazine for 1-methyl piperazine. The structure assignment was supported by NMR, infrared and mass spectroscopy and elemental analysis (520.85).

Analysis calc. for $C_{29}H_{48}N_2O_2S_2$: C, 66.88; H, 9.29; N, 5.38. Found C, 66.86; H, 9.61; N, 5.49.

EXAMPLE 22

(±)
1-(4-acetylphenyl)-4-[2-[[2S*-[[3,5-bis(1,1-dimethylethyl)-4-hydroxyphenyl]thio]-1R*-methylpropyl]thio]-1-oxoethyl]piperazine

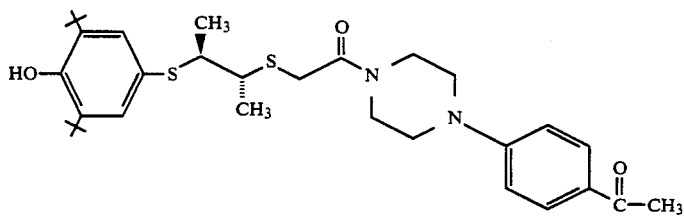

The title compound was prepared by the method of Example 20 by substituting the compound of Example 9 for the compound of Example 4 and 4'-piperazinoacetophenone for 1-methyl piperazine. The structure assignment was supported by NMR, infrared and mass spectroscopy.

What is claimed is:

1. A compound of the formula:

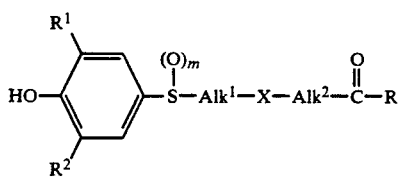

wherein $R^1$ and $R^2$ are the same or different and independently represent tert-alkyl or phenyl; $Alk^1$ represents straight or branched chain alkylene of 1 to 10 carbon atoms; X represents sulfur or oxygen; $Alk^2$ represents straight or branched chain alkylene of 1 to 4 carbon atoms; m is 0 or 1; and R represents:

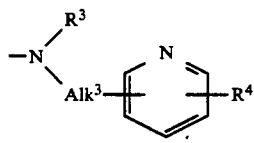

wherein $R^3$ is hydrogen or alkyl of 1 to 4 carbon atoms; $Alk^3$ is straight or branched chain alkylene of 1 to 4 carbon atoms; and $R^4$ is hydrogen or alkyl of 1 to 4 carbon atoms, or a pharmaceutically acceptable salt or stereoisomer or geometric isomer thereof.

2. A compound according to claim 1 of the formula:

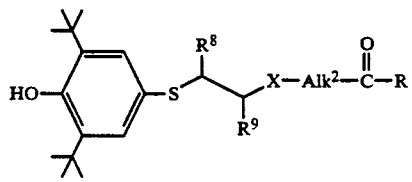

or a pharmaceutically acceptable salt or stereoisomer or geometric isomer thereof, wherein $R^8$ and $R^9$ are alike or different and are hydrogen or alkyl of 1 to 4 carbon atoms.

3. A compound according to claim 1 wherein $R^1$ and $R^2$ are tert-alkyl.

4. A compound according to claim 1 which is 2-[[2-[3,5-bis(1,1-dimethylethyl)-4-hydroxyphenyl]thio]ethyl]thio]-N-(2-pyridinylmethyl)acetamide.

5. A compound according to claim 1 which is (±) 2S*-[2-[[3,5-bis(1,1-dimethylethyl)-4-hydroxyphenyl]-thio]-1R*-methylpropoxy]-N-methyl-N-[2-(2-pyridinyl)ethyl]acetamide.

6. A compound according to claim 1 which is 2-[[2-[[3,5-bis(1,1-dimethylethyl)-4-hydroxyphenyl]thio]ethyl]thio]-N-(3-pyridinylmethyl)acetamide.

7. A compound according to claim 1 which is 3-[[2-[[3,5-bis(1,1-dimethylethyl)-4-hydroxyphenyl]thio]ethyl]thio]-N-methyl-N-[2-(2-pyridinyl)ethyl]propanamide.

8. A compound according to claim 1 which is (±) 2S*-[[[2-[[3,5-bis(1,1-dimethylethyl)-4-hydroxyphenyl]-thio]-1R*-methylpropyl]thio]-N-(4-pyridinylmethyl)acetamide.

9. A compound of claim 1 wherein $R^1$ and $R^2$ represent tert-alkyl; $Alk^1$ represents straight or branched chain alkylene of 1 to 4 carbon atoms; $Alk^2$ represents straight or branched chain alkylene of 1 to 2 carbon atoms; m is 0; $R^3$ is hydrogen or alkyl of 1 to 2 carbon atoms; $Alk^3$ is straight or branched chain alkylene of 1 to 2 carbon atoms; and $R^4$ is hydrogen.

10. A pharmaceutical composition for the treatment of inflammation and allergy conditions comprising a therapeutically effective amount of a compound according to claim 1 and a pharmaceutically acceptable carrier.

11. A pharmaceutical composition for the treatment of inflammation and allergy conditions comprising a therapeutically effective amount of a compound according to claim 2 and a pharmaceutically acceptable carrier.

12. A pharmaceutical composition according to claim 10 wherein said compound is:

2-[[2-[3,5-bis(1,1-dimethylethyl)-4-hydroxyphenyl]thio]-ethyl]thio]-N-(2-pyridinylmethyl)acetamide;

(±) 2S*-[2-[[3,5-bis(1,1-dimethylethyl)-4-hydroxyphenyl]thio]-1R*-methylpropoxy]-N-methyl-N-[2-(2-pyridinyl)ethyl]-acetamide;

2-[[2-[[3,5-bis(1,1-dimethylethyl)-4-hydroxyphenyl]thio]-ethyl]thio]-N-(3-pyridinylmethyl)acetamide;

3-[[2-[[3,5-bis(1,1-dimethylethyl)-4-hydroxyphenyl]thio]-ethyl]thio]-N-methyl-N-[2-(2-pyridinyl)ethyl]-propanamide; or (±) 2S*-[[[2-[[3,5-bis(1,1-dimethylethyl)-4-hydroxyphenyl]-thio]-1R*-methylpropyl]thio]-N-(4-pyridinylmethyl)acetamide.

13. A method of treating an inflammatory or allergic condition comprising administering to a mammal in need of such treatment a therapeutically effective amount of a compound according to claim 1.

14. A method of treating an inflammatory or allergic condition comprising administering to a mammal in need of such treatment a therapeutically effective amount of a compound according to claim 2.

15. A method of inhibiting 5-lipoxygenase comprising administering to a mammal in need of such treatment a therapeutically effective amount of a compound according to claim 1.

16. A method of treating asthma comprising administering to a mammal in need of such treatment a therapeutically effective amount of a compound according to claim 1.

17. A method of treating psoriasis comprising administering to a mammal in need of such treatment a therapeutically effective amount of a compound according to claim 1.

18. A method according to claim 13 wherein said compound is:

2-[[2-[3,5-bis(1,1-dimethylethyl)-4-hydroxyphenyl]thio]-ethyl]thio]-N-(2-pyridinylmethyl)acetamide;

(±) 2S*-[2-[[3,5-bis(1,1-dimethylethyl)-4-hydroxyphenyl]thio]-1R*-methylpropoxy]-N-methyl-N-[2-(2-pyridinyl)ethyl]-acetamide;

2-[[2-[[3,5-bis(1,1-dimethylethyl)-4-hydroxyphenyl]thio]-ethyl]thio]-N-(3-pyridinylmethyl)acetamide;

3-[[2-[[3,5-bis(1,1-dimethylethyl)-4-hydroxyphenyl]thio]ethyl]thio]-N-methyl-N-[2-(2-pyridinyl)ethyl]-propanamide; or (±) 2S*-[[[2-[[3,5-bis(1,1-dimethylethyl)-4-hydroxyphenyl]thio]-1R*-methylpropyl]thio]-N-(4-pyridinylmethyl)acetamide.

19. A method of modulating superoxide generation comprising administering to an animal in need of such treatment an amount of a compound according to claim 1 which is effective to stimulate or inhibit superoxide generation.

* * * * *

UNITED STATES PATENT AND TRADEMARK OFFICE
CERTIFICATE OF CORRECTION

PATENT NO. : 5,298,514
DATED : March 29, 1994
INVENTOR(S) : Mueller, et al.

It is certified that error appears in the above-indentified patent and that said Letters Patent is hereby corrected as shown below:

Column 1, line 43, reading "$E_4$ $LTC_4$" should read -- $E_4$. $LTC_4$ --.

Column 6, line 1, the formula reading

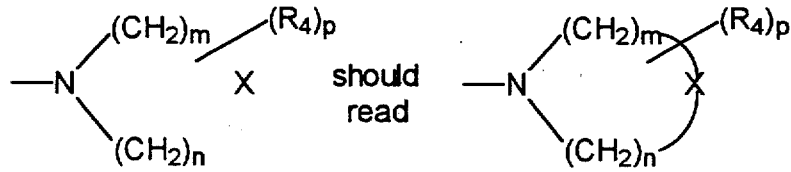

Column 6, line 10, reading "$N-R_4$, and" should read -- $N-R_4$, O and --.

Column 12, line 42, should read -- (±)[2S*-[[3,5-bis(1,1-dimethylethyl)-4-hydroxyphenyl]thio]-1R*-methylpropoxy]acetic acid --.

Signed and Sealed this

Fifteenth Day of August, 1995

Attest:

BRUCE LEHMAN

Attesting Officer    Commissioner of Patents and Trademarks